United States Patent
Kawai et al.

(10) Patent No.: US 6,255,107 B1
(45) Date of Patent: Jul. 3, 2001

(54) ANTIBODIES, PRODUCTION METHOD OF THE ANTIBODIES, HYBRIDOMAS WHICH PRODUCE THE ANTIBODIES, PRODUCTION METHOD OF THE HYBRIDOMAS AND ANTIGEN PROTEINS RECOGNIZED BY THE ANTIBODIES

(75) Inventors: Makoto Kawai, Nagoya; Tadashi Okada, Nisshin; Fukiko Atsumi, Nagoya, all of (JP)

(73) Assignee: Medical & Biological Laboratories Co., Ltd., Nagoya (JP)

(*) Notice: Subject to any disclaimer, the term of this patent is extended or adjusted under 35 U.S.C. 154(b) by 0 days.

(21) Appl. No.: 09/229,932

(22) Filed: Jan. 13, 1999

(30) Foreign Application Priority Data

Jan. 14, 1998 (JP) .................................... 10-005908

(51) Int. Cl.[7] .............. C12N 5/12; C12N 5/16; C07K 16/00; C12P 21/08
(52) U.S. Cl. ................ 435/326; 435/346; 530/388.1; 530/388.7
(58) Field of Search .............. 530/387.1, 388.1, 530/388.7; 435/326, 346

(56) References Cited

FOREIGN PATENT DOCUMENTS 243 713 A1  3/1987 (DE).

OTHER PUBLICATIONS

Kishimoto et al. Leukocyte Typing II, Garland Publ., NY & London, pp. 816, 817, 1046, 1047, 1997.*
Buckley et al. J. Pathol. vol. 186, pp. 67–74, 1998.*
Schlossman et al. Leukocyte Typing V., vol. 2, Oxford Univ. Press, Oxford, NY & Tokyo, pp. 1920–1921, 1995.*
Campbell, Alisa M. Monoclonal Antibody Technology, Elsevier Science Publishers B.V., NY, pp. 1–32. 1985.*
Czarnetzki B M et al, Immunology, "Development of human connective tissue mast cells from purified blood monocytes.", 1984, pp 549–554.
Odarjuk J et al, International Archives of Allergy and Applied Immunology, "Investigation of mast cell differentiation in vivo by use of monoclonal antibodies.", 1989, pp 261–266.
Mayrhofer G et al, Immunology and Cell Biology, "Specificity of a mouse monoclonal antibody raised against acute myeloid leukaemia cells for mast cells in human mucosal and connective tissues.", 65 R (1.3) 1987, pp 241–250.
O'Doherty U et al, Dendritic Cells in Fund. & Clin. Immunol., "Tolerizing mice to human leukocytes: a step toward the production of monoclonal antibodies specific for human dendritic cells.", 1993, pp 165–172.

* cited by examiner

Primary Examiner—Christina Y. Chan
Assistant Examiner—Marianne DiBrino
(74) Attorney, Agent, or Firm—Davis & Bujold, P.L.L.C.

(57) ABSTRACT

The invention is related to antibodies which specifically react with connective tissue type-human mast cells, a production method of the antibodies, hybridomas which produce the antibodies, a production method of the hybridomas and antigen proteins recognized by the antibodies. After cord blood cells were cultured in the presence of SCF and IL-6, they were further cocultured with primary culture of human skin fibroblasts, and connective tissue type-human mast cells were thus obtained. A rat was immunized using the cells, hybridomas were prepared and selected by an ordinary method, and novel monoclonal antibodies were harvested from the culture supernatant of the selected hybridomas. The monoclonal antibodies specifically reacted with connective tissue type-human mast cells.

2 Claims, 3 Drawing Sheets

M.W   MOLECULAR WEIGHT MARKER
(1)   ANTIGEN: POSITIVE CELL
      PRIMARY ANTIBODY: CLONE 5C12
(2)   ANTIGEN: POSITIVE CELL
      PRIMARY ANTIBODY: NORMAL RAT SERUM
(3)   ANTIGEN: NEGATIVE CELL
      PRIMARY ANTIBODY: CLONE 5C12
(4)   ANTIGEN: NEGATIVE CELL
      PRIMARY ANTIBODY: NORMAL RAT SERUM

ANTIBODIES, PRODUCTION METHOD OF THE ANTIBODIES, HYBRIDOMAS WHICH PRODUCE THE ANTIBODIES, PRODUCTION METHOD OF THE HYBRIDOMAS AND ANTIGEN PROTEINS RECOGNIZED BY THE ANTIBODIES

BACKGROUND OF THE INVENTION

1 Field of the Invention

This invention relates to antibodies, a production method of the antibodies, hybridoma strains which produce the antibodies, a production method of the hybridomas and antigen proteins recognized by the antibodies.

2 Background Art

In case of allergic disease such as the bronchial asthma or the allergic rhinitis, at first, the production of IgE specific to the antigen is induced. Various mediators such as histamine, eosinophil chemotactic factor in allergy (ECF-A), leukotrienes, platelet-activating factor (PAF) and thromboxane are produced and released from mast cells, basophils and the like, activated by the induced IgE. As the result, allergic diseases are induced.

Specifically, mast cells play an important role in tissues for the induction of allergic diseases by releasing these chemical mediators. The mast cells are recognized in the periphery of blood vessels of every tissue in the body. Especially, the cells densely distribute in the area beneath the epidermis, the respiratory airways, the gastrointestinal tract mucosa and the like. These mast cells differ in the phenotypes depending on the tissues where they distribute. In mice, the mast cells are divided into two types, connective tissue-type mast cells and mucosal mast cells (MMC), depending on the existing area, the size, fc-malin sensitivity, the contained chemical mediator and the like, Though there is no distinct difference such as MMC and CTMC in human mast cells, they are differentiated into tryptase positive cell (MC-T) and both tryptase and chymase positive cells (MC-TC). MC-T distributes in the lung tissue and the gastrointestinal tract mucosa, while MC-TC distributes in the skin tissue.

Human mast cells, unlike cells of other leukocytes, leave bone marrow for peripheral environment as pluripotent stem cells, and may differentiate into MC-T or into MC-TC following adhesion to either lung or skin fibroblast. Studies on differentiation and proliferation of human mast cells were not advanced compared with those of mouse mast cells. The reason is that the culture method of human mast cells in vitro was not established. When human bone marrow cells were cultured in the presence of IL-3, the finally induced products were mainly basophils and mast cells could not obtained. In 1989, Furitsu et al. succeeded in culturing human mast cells by a coculture of cord blood mononuclear cells with mouse fibroblasts. Subsequently, a factor participating in differentiation and proliferation of mast cells was identified on fibroblasts (stem cell factor, called SCF hereinafter). After its cDNA was cloned, the culture of human mast cells from mononuclear cells in the bone marrow, peripheral blood or embrio liver became possible by using SCF.

In order to make clear the mechanism of allergic inflammation and to provide with an appropriate cure thereof, it is necessary to obtain these mast cells from differing tissues in pure state and to know their properties distinctly.

Heretofore, to obtain these mast cells, specific to tissues, mast cells have been isolated from each tissue by the enzymatic method. But according to the method, the quantity of isolated cells was limited, for it was technically difficult to purify only the mast cells specific to a tissue.

Nowadays, various differentiated cells are obtained in large quantities by cell culture, and cell surface antigens specific to cells are made clear. Therefore, technologies for purifying homogeneous cells by using antibodies against these antigens are now well established. But concerning to mast cells, especially to connective tissue type-mast cells (MT-TC) distributed in the skin, neither specific cell surface antigens nor antibodies which recognize the antigens is obtained.

SUMMARY OF THE INVENTION

An object of the invention is to provide antibodies which specifically react with the MC-TC.

Another object of the invention is to provide a production method of the antibodies.

Still another object is to provide hybridomas which produce the antibodies.

A further object is to provide a production method of the same and antigen proteins recognized by the antibody.

To attain these and other objects, in one aspect of the invention, the antibodies are characterized by specifically reacting with the cell surface antigens which manifest specifically in the connective tissue type-human mast cells. Among such antibodies, for example, antibodies produced by a novel hybridoma ahMC5C12 accession No. FERM BP-6070) deposited Aug. 21, 1997 at the National Institute of Bioscience and Human-Technology Agency of Industrial Science and Technology, Michio Oishi, Ph.D., DIRECTOR GENERAL, 1–3, Higashi 1-chome, Tsukuba-shi, Obaraki-ken 305, JAPAN are obtained. By using such antibodies, the MC-TC which were difficult to separate in the past can be easily isolated among tissues and used to disclose the role of mast cells in the allergic reaction. By applying the antibody to immunohistochemistry and flow cytometry, it is possible to evaluate the distribution, quantity change and morphological abnormality of mast cells. Furthermore, this, mast cell specific antibody is of value in the diagnosis, understanding of pathophysiology, and treatment of allergic diseases.

For example, the antibodies can be obtained by applying the following three processes:

(1) Tryptase positive cells of human mast cells are prepared by culturing cord blood mononuclear cells in the presence of a factor related with the differentiation and multiplication of mast cells manifested on fibroblasts and interleukin-6. Thus obtained cells are cocultured with a primary culture of fibroblast obtained from human skin tissues, to get connective tissue type-human mast cells which are both tryptase and chymase positive cells.

(2) Human cord blood cells are injected to a newborn mammal (except human neonate), to obtain immunological tolerance for all antigens in the cells. Subsequently, the connective tissue type-human mast cells prepared in the first process are injected to the mammal for immunization Hybridomas are prepared by fusing antibody producing cells from the sensitized mammal with myeloma cells.

(3) Clones which are producing antibodies that react with the connective tissue type-human mast cells are selected among the hybridoma cells prepared in the second process. The clones are cultured and antibodies that react with the connective tissue type-human mast cells are obtained by purifying the supernatant of the culture.

The hybridomas of another aspect of the invention are characterized by producing the aforementioned antibodies.

Such hybridomas are, for example, the aforementioned hybridoma clones, ahMC5C12, which can be obtained by the following procedure: Human cord blood cells are injected, for example, to a newborn mammal (except human neonate), to obtain immunological tolerance for all antigens in the cells. Subsequently, the connective tissue type-human mast cells are injected to the mammal for immunization. The hybridomas are prepared by fusing antibody producing cells obtained from the immune sensitized mammal with myeloma cells. Clones which are producing antibodies that react specifically with the connective tissue type-human mast cells are selected among the hybridomas. The clones are cultured and a hybridoma cell line is established.

The antigen proteins of the further aspect of the invention are characterized by manifesting specifically on cell surfaces of connective tissue type-human mast cells and by being recognized specifically by the antibodies of the invention. The molecular size of the antigen protein is, for example, from 90 kD to 110 kD and the protein does not exist on the surface of blood cell in the peripheral blood. By using such antigen proteins, new antibodies which recognize different epitopes of the same antigen of human mast cells can be obtained and the relation thereof with various allergic diseases can be recognized.

BRIEF DESCRIPTION OF DRAWING FIGURES

The present invention will be described, by way of example, with reference to the accompanying drawings, in which.

DETAILED DESCRIPTION OF THE PREFERRED EMBODIMENTS

Figure 1:
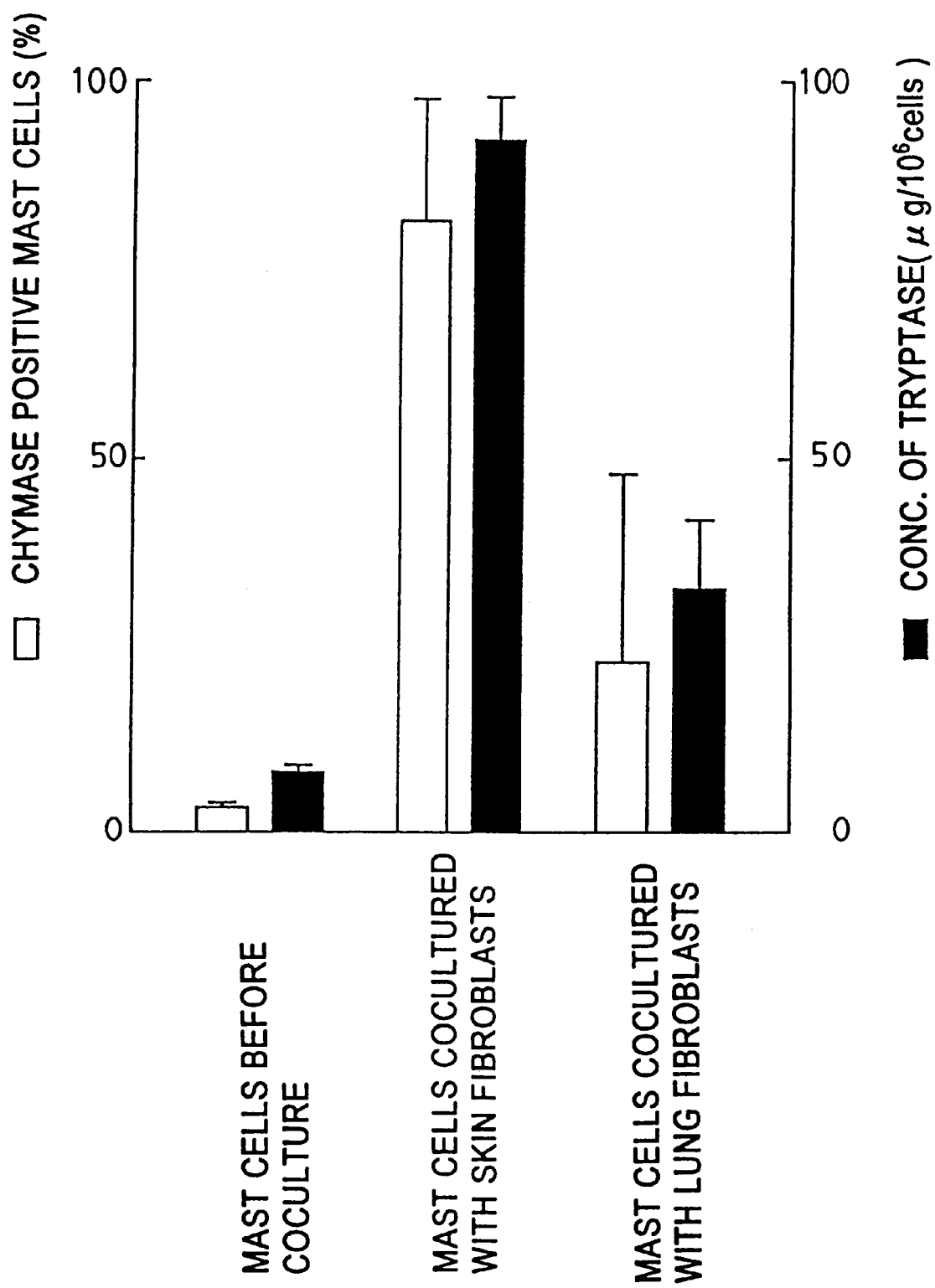
FIG. 1 is a graph showing the ratio of chymase positive mast cells and measured values of tryptase concentration for the mast cells before and after coculture.

Antibodies which Specifically React with Connective Tissue Type-Human Mast Cells and Hybridomas which Produce the Antibodies A. Antigens (Culture of Connective Tissue Type-Human Mast Cell)

Mast cells in human skin tissues are MC-TCs which contain both tryptase and chymase in their granules. MC-TCs are thought to be the most differentiated connective tissue type-cell and are cells indispensable for studying mast cells. In recent years, SCF was discovered as a growth factor of the mast cells produced by fibroblasts and the process of differentiation of human mast cells became to be studied using culture system. The inventors obtained cultured human mast cells by culturing stem cells (CD34+cells) in the peripheral blood in the presence of SCF, but the mast cells obtained by such method were mostly T-type mast cells or MC-T which contained only tryptase and no chymase in their granules. However, the inventors succeeded in differentiating MC-T into MC-TC by coculturing MC-T with the primary culture of fibroblasts from human skin tissues (The 46th General Meeting of the Japanese Society of Allergology, Nov. 1, 1996, Allergy Vol. 45, 1005).

B. Preparation of Antibodies

In order to obtain antibodies specific to the differentiated MC-TC, for example, the immunotolerance method is used. Specifically, an infant rat 4 days after birth is injected to its abdominal cavity with cells from human umbilical cord blood cultured for 2 weeks to ablate the ability of producing antibodies to all antigens of the injected cells to induce production of antibodies. Then, 1.5 months later, the rat is injected to its abdominal cavity with MC-TC for immunization. Further, after immunization is repeated every two weeks, spleen cells are taken out and fused with myeloma strains etc. by a known method using polyethylene glycol, Sendai virus, electric pulse or the like, to prepare hybridomas. Subsequently, the clones which are producing antibodies to be connected to MC-TCs are selected and cultured. By purifying the culture supernatant of the selected clones, monoclonal antibodies can be obtained. For the purification, any known method such as salting out, ion exchange chromatography, affinity chromatography or the like may be used.

Alternatively, the aforementioned antibodies may be prepared using gene engineering method. For example, spleens are taken out from immunized animals, a cDNA library is formed based on them, clones which are producing antibodies that react with MC-TCs are screened, the clones are cultured and the aimed antibodies may be obtained from the mixture of the culture.

Antigen Proteins Recognized by Aforementioned Antibodies

MC-TC antigen proteins can be obtained using the antibodies prepared above. For example, after the cells of MC-TC are homogenized and membrane fragments were separated by ultracentrifugal method, the antigen proteins can be prepared by purifying the antigen with the capillary electrophoresis and Western blot.

Embodiment 1

Culture of Cord Blood Mononuclear Cells

Cord blood treated with heparin was layered over the Ficoll Hypaque solution (specific gravity; 1.077, Sigma Inc.), centrifuged at 300×G for 30 min. to separate the mononuclear cells, which were suspended in a culture medium, RPMI1640 (Nissui Seiyaku), containing 10% of FBS (Gibco BRL), 50 $\mu$M of 2-mercaptoethanol, 4 mM of L-glutamine, 100 U/ml of penicillin and 50 $\mu$g/ml of streptomycin. The concentration of the mononuclear cells in the suspension was adjusted to 5×10$^6$/ml, the suspension was poured into a collagen coated culture dish (diameter: 10 cm, Iwaki Glass), SCF (100 ng/ml, PeproTech Inc., Rochy Hill, N.J.) and IL-6 (50 ng/mL, PeproTech Inc.) were added to it, cultured for 2 weeks and two week-cultured cells containing neutrophils, lymphocytes, macrophages, basophils and precursor cells of mast cell were obtained.

Embodiment 2

Culture of MC-TC

The cord blood mononuclear cells were cultured in the presence of 100 ng/ml of SCF and 50 ng/ml of IL-6 for 6 weeks and when the human mast cells became predominant, that is, when the number of human mast cells reached the order of 10$^6$, the mast cells were further cocultured with a primary culture of human fibroblasts. Specifically, the human mast cells were transferred to a monolayer of human fibroblasts from either skin or lung tissues and cultured for 2 months in the presence of 50 ng/ml SCF.

The ratio of chymase positive mast cells and the concentration of tryptase were measured for the mast cells before and after the coculture. The result shown in FIG. 1 shows that before the coculture of mast cells, i.e. for the human mast cells cultured for 10–16 weeks in the presence of SCF and IL-6 (the left end of the graph in FIG. 1), the ratio of chymase positive cells and the concentration of tryptase were both very low, while those for the human mast sells after cocultured with human fibroblasts for 6–8 weeks (the center of the graph in FIG. 1) and those for the human mast cells cocultured with lung fibroblasts (the right end of the graph in FIG. 1) showed remarkable increases, especially for the human mast cells cocultured with skin fibroblasts.

The mast cells cultured for 15 weeks in the presence of SCF and IL-6 and the mast cells cocultured with skin fibroblasts for 2 months after having been cultured for 6 weeks were stained using antibodies against tryptase and those against chymase, with the result that in case of tryptase, both mast cells were confirmed to have been wholly stained, while in case of chymase, most cells cocultured with fibroblasts were confirmed to have been stained but cells which were not cocultured were confirmed to have been only partly stained. The results show that MC-T are differentiated into MC-TC by the coculture.

As described above, connective tissue type-human mast cells, or MC-TC, proved to be obtained by culturing code blood cells in the presence of SCF and IL-6 and subsequently coculturing them with the primary culture of human skin fibroblasts.

Embodiment 3
Immunization and Production of Antibodies
1) Immunization of Rat

An infant rat 4 days after birth was injected to its abdominal cavity with the cells obtained from cord blood cells cultured for 2 weeks in Embodiment 1 ($10^6$ cells/0.1 ml) to ablate the induction ability of antibody production for all antigens in the cells by inducing immunotolerance. Then, 1.5 months later, the rat is injected to its abdominal cavity with both the MC-TC ($10^6$ cells/0.10 ml) obtained in aforementioned Embodiment 2 and complete adjuvant to sensitize the rat. Further, the rat was injected to its abdominal cavity with the cells alone two times every two weeks. The spleen was taken out 4 days after the final immunization and the cell fusion was carried out as follows.

2) Selection and Preparation of Monoclonal Antibodies Specific to Antigens of Human Mast Cell Surfaces Spleen cells (10 parts) taken out from the rat and myeloma cells (1 part) were mixed, added with 50% polyethylene glycol 1500 as a fusion accelerator and cell fusion was carried out. After the cell fusion, the cells were suspended in HAT culture medium containing 10% bovine serum in a way such that the cell concentration becomes $5\times10^5$ cells/ml for spleen cells, and distributed to a 96 well microtiter plate by 200 µl for every well.

The hybridomas were cultured in a $CO_2$ incubator (5% $CO_2$, 37° C.), and grown in HAT medium. Screening of the hybridomas of spleen cells and myeloma cells was carried out. The cells were then adapted and cultured in (Iscove's modified Dulbecco's medium) IMDM supplemented with 10% FCS (Fetal Calf Serum).

Among antibodies in the culture supernatant of the hybridomas, by using MC-TC separated from skin lesion of mastocytoma as antigens, cloves which produce antibodies specific to the antigens were separated by the fluorescent antibody method and named ahMC5C12 (FERM BP-6070). The harvested clone cells were suspended in 90% bovine serum containing 10% DMSO and kept in liquidified nitrogen.

3) Preparation of Monoclonal Antibodies

The monoclonal antibodies, specific to mast cell surface antigens produced by the clone, were harvested by growing the ahMC5C12 in the abdominal cavity of a nude mouse and purifying the antibody.

Embodiment 4
Confirmation of Specificity of Antibodies
1) Confirmation of Specificity by Staining (1) MC-TC smear was fixed with Carnoy's fixative, added with the culture supernatant of the clones ahMC5C12 obtained in aforementioned Embodiment 3, reacted at 37° C. for 40 minutes, washed with water, reacted with anti-rat immunoglobulin (IgG+IgM) labeled with FITC for 40 minutes and washed with PBS. The smear was counterstained with Evans blue and confirmed to have been stained. Instead of said culture supernatant, PBS was used as a control, but no staining was observed on said smear.

(2) The smear of cord blood mononuclear cell was fixed with Carnoy's fixative, added with the culture supernatant of the clone ahMC5C12 obtained in aforementioned Embodiment 3 and treated in the same way as above, but stained cells were not observed. The smear contained 0.4% basophil among the total cells of $2\times10^4$. The result suggests that epitope is not the IgE receptor.

(3) The cord blood mononuclear cells were cultured in the presence of SCF and IL-6 for 3 weeks and 6 weeks, respectively, in the same way as above. In both cases, cells to be stained were not observed In average, the constitution of cells cultured for 3 weeks was of the constitution ratio in Table 1. Therefore, it was suggested that the antibodies do not react with any of the cells in Table 1. The constitution of cells cultured for 6 weeks is shown in Table 2. This suggests that the antibodies do not react with immature human mast cells, and thus epitope is not the c-kit receptor which binds SCF. Furthermore, since the human mast cells (MC-T) contain tryptase, it was suggested that the antibodies neither react with tryptase. In addition, as it will be explained later, since the molecular weight of the antigen is 90 to 110 kD, the antibodies are thought not to react with chymase with the molecular weight of 30 kD.

TABLE 1

| Consideration of cells after culturing for 3 weeks | |
|---|---|
| Myeloid Cells (myeblast, promelocyte, metamyelocyte, beutrophil) | 65% |
| Lymphocyte | 12 |
| Macrophage | 4 |
| Basophil | 1.5 |
| Mast cell | 7 |
| Lymphoid cell (blasts) | 10.5 |

TABLE 2

| Constitution of cells after culturing for 6 weeks | |
|---|---|
| Mast cell (ratio of MC-T is equal to or more than 90%) | 71.2% |
| Basophil | 1 |
| Lymphocyte | Most of the remainder |
| Macrophage, Neutrophil | Trace |

(4) A smear sample of normal human peripheral blood was prepared and treated in the same way as above. Staining was not observed for any cells in the human peripheral blood.

(5) A frozen section of human normal skin tissue, as a sample, was stained with the antibody and compared with the result of staining by Toluidine Blue. Then, cells having granules which are stained purple because of metachromasia were stained by the immunofluorescence technique. Mucosal mast cells were not stained by the same method. These facts show that the antibody specifically recognizes the TC-type mast cells.

From the aforementioned (1)–(5), it was shown that the antibodies are not those which react with any of IgE receptor, c-kit receptor, tryptase and chymase, but those which recognize the connective tissue type-human mast cells or MCTC. Also, it was proved that the antigen expressed on MC-TC recognized by the antibody does not exist on the surface of cells in human peripheral blood.

2) Confirmation of Specificity by Flow Cytophotometry

MC-TC (50 parts) were added with the ascites fluid (antibody) (1 part) from a nude mouse injected with the hybridoma ahMC5C12 into its abdominal cavity, while other MC-TC as the control (50 parts) were added with serum of a normal rat (1 part). Both cells added with the antibody or with serum of normal rat, respectively, were incubated for 1 hour in an ice-cold bath. Then, they were centrifuged at 1000 rpm for 10 minutes and, after their supernatants were discarded, suspended in PBS with 1% BSA. They were centrifuged again, suspended in 0.8 ml of PBS with 1% BSA, and reacted with rat immnoglobulin labeled with FITC (IgG+IgM) (goat) at 25° C. for 20 minutes. After the reaction was over, they were centrifuged at 800 rpm for 10 minutes, washed 3 times with PBS with 1% BSA. Expression of the antigen on the surface of MC-TC was analyzed using FACScan (Becton Dickinson Inc.).

Figure 2B:
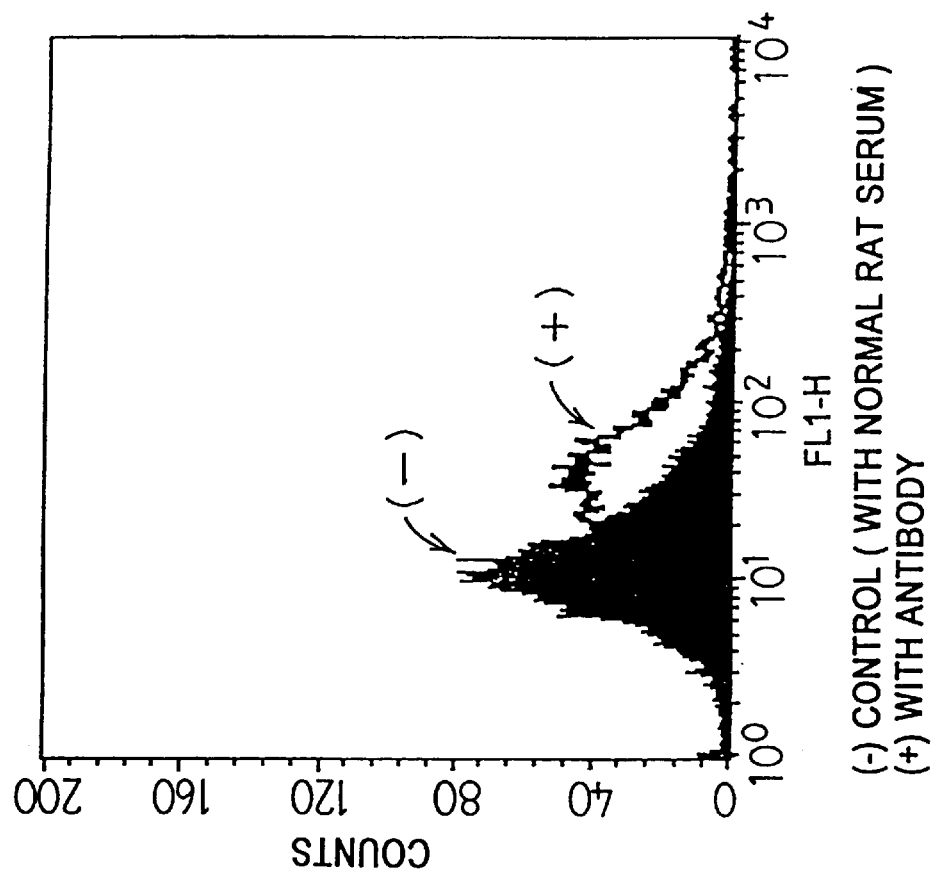
FIG. 2A and 2B are graphs showing the result of flow cytometry.
Figure 2A:
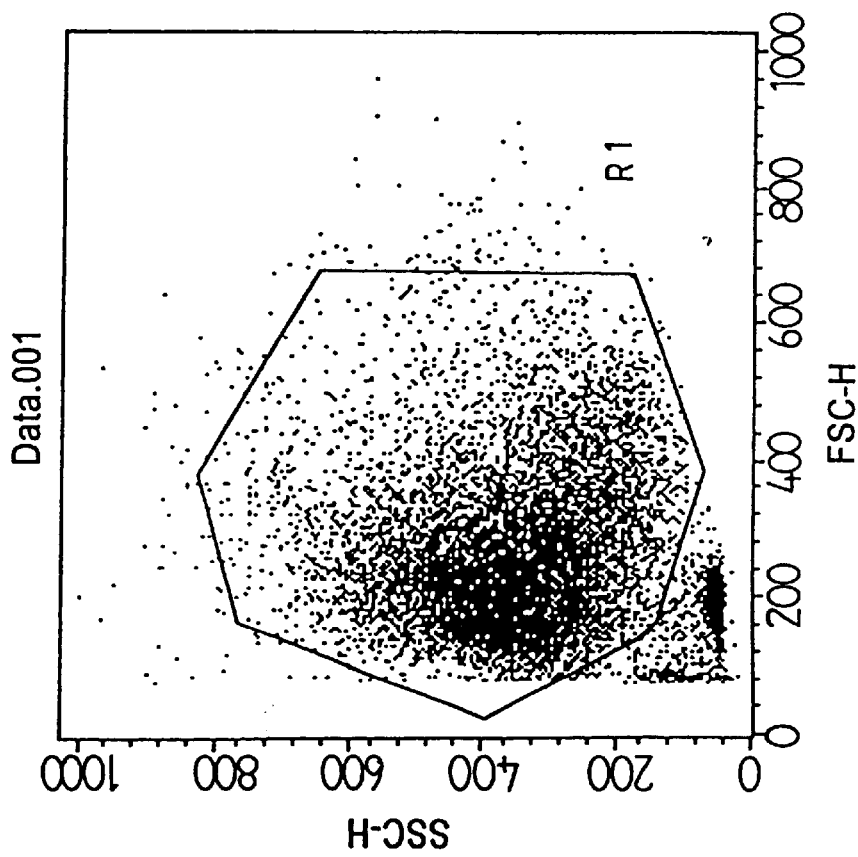

The results were shown in FIG. 2A and FIG. 2B. In FIG. 2A, the abscissa shows the size of cells and the ordinate is a scale showing the roughness of the cell surface. Since mast cells are large and heavily granulated, they are main cells in the figure and thought to distribute within a heptagonal frame, differing from lymphocytes. FIG. 2B shows distributions of cells in the frame of FIG. 2A vs. the strength of fluorescence indicated on the abscissa. It was also shown by the photograph of immunofluorescence technique which is not shown here that there are varieties of cells among mast cells, ranging from strongly stained cells to weakly stained cells when stained with the antibody. In case of FACS, there was also shown a broad distribution of the strength of fluorescence, ranging from 3 to 500. These facts may suggest that the quantity of expressed antigen changes with the degree of cell differentiation. Also, the peak of cell distribution is moved by the reaction with the antibodies, which shows that the antibodies react with antigens which exist on surfaces of TC type-mast cells.

Since cells were stained in this way while they were alive, without fixation, the antibody is thought to react with antigens which were expressed on the cell surface. The antigen is thought to be a novel differentiation marker which is expressed on the cell surface, depending on the differentiation of mast cells (MC-T→MC-TC or mucosal type→connective tissue type).

3) Confirmation of Specificity by Western Blotting and Molecular Weight of Corresponding Antigen The positive cells (MC-TC) were mixed with an equal quantity of SDS-PAGE sample buffer added with 2-ME, boiled at 100° C. for 5 minutes to make a cell solution, which was used as antigens. SDS- polyacrylamide gel electrophoresis (SDS-PAGE) was carried out using the antigen according to Laemmli method. The composition of SDS-PAGE sample buffer added with 2-ME is shown in the following Table 3.

TABLE 3

| SDS-PAGE sample buffer added with 2-ME | |
|---|---|
| C solution for electrophoresis | 6.25 ml |
| SDS | 1 g |
| 2-Mercapto ethanol | 2.5 ml |
| Bromophenol Blue | 0.5 mg |
| Glycerol | 5 ml |
| Deionized water | 36.25 ml |

The electrophoresis was carried out using 4.5% condensed gel and 12.5% separation gel. After the sample was separated according to an ordinary method, it was blotted to a nitrocellulose membrane, reacted with primary antibody (ascites fluid obtained by inoculating the hybridoma ahMC5C12 to the abdominal cavity of a nude mouse (refferred to as "the antibody") or serum of normal rat. Anti-rat immunoglobulins labeled with peroxidase mere used as the secondary antibodies and the specific band was detected using aminobenzidine as a substrate. Similarly, Western blotting was carried out using cells obtained by culturing human cord cells for 2 weeks (negative cells).

Figure 3:
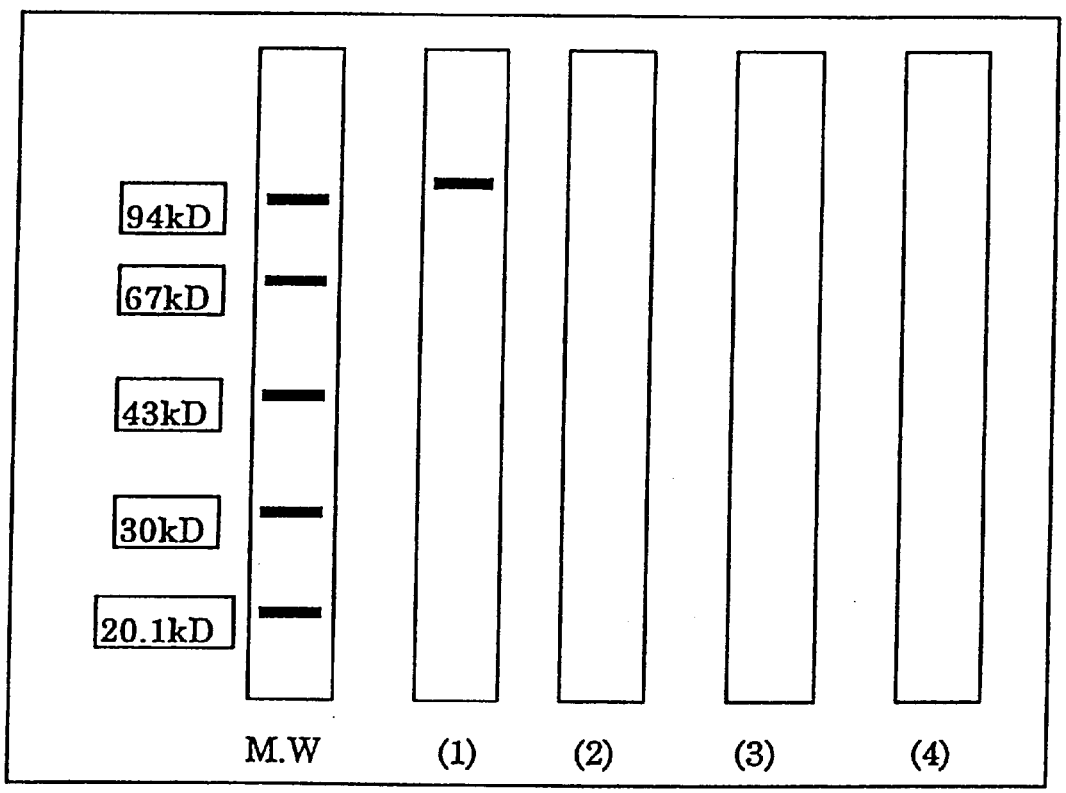
FIG. 3 is a graph showing the result of Western blotting.

The result was shown in FIG. 3. When the MC-TC (positive cells) were reacted with "the antibodies" as the primary antibodies, a band was detected at the molecular weight of ca.100 kD (90 kD–110 kD). But when negative cells were used as antigens or when normal rat serum was used as the primary antibody, no band was detected. These facts show that the antibody specifically react with antigens which are specifically expressed on MC-TC.

What is claimed is:

1. Antibody reacting with a cell surface antigen which is expressed solely on tryptase and chymase positive human mast cells wherein said antibody is produced by hybridoma clone ahMC5C12 (Accession No. FERM BP6070).

2. Hybridoma which produces an antibody reacting with a cell surface antigen which is expressed solely on tryptase and chymase positive human mast cells, wherein said hybridoma is hybridoma clone ahMC5C12.

* * * * *